United States Patent [19]

Gaffar

[11] Patent Number: 4,975,423

[45] Date of Patent: Dec. 4, 1990

[54] INHIBITION OF TUMOR DEVELOPMENT

[75] Inventor: Abdul Gaffar, Somerset, N.J.

[73] Assignee: Colgate-Palmolive Company, New York, N.Y.

[21] Appl. No.: 351,332

[22] Filed: May 3, 1989

Related U.S. Application Data

[63] Continuation of Ser. No. 726,545, Apr. 24, 1985, abandoned, which is a Continuation-in-Part of Ser. No. 625,067, June 24, 1984, abandoned.

[51] Int. Cl.[5] .................... A01N 57/00; A01N 59/26; A61K 31/66; A61K 33/42
[52] U.S. Cl. .................................. 514/108; 424/601; 424/602; 424/604; 424/606
[58] Field of Search ................ 514/108; 424/601, 602, 424/604, 606

[56] References Cited

U.S. PATENT DOCUMENTS 4,634,691  1/1987  Hedglin et al. .................... 514/108

*Primary Examiner*—Nathan M. Nutter
*Attorney, Agent, or Firm*—Murray M. Grill; Robert L. Stone

[57] ABSTRACT

Non-toxic water-soluble pharmaceutically acceptable compound derivative of peroxydiphosphoric acid when administered orally or systemically supplements inhibition of malignant myeloma carcinoma tumor development of tumor cells in vitro and actual tumor development in vivo in warm blooded animals.

16 Claims, No Drawings

INHIBITION OF TUMOR DEVELOPMENT

This application is a continuation of application Ser. No. 726,545 filed Apr. 24, 1985, now abandoned, which is a Continuation-in-Part of Application Ser. No. 625,067, filed June 24, 1984, now abandoned.

This invention relates to the supplementing inhibition of tumor development with respect to tumor cells in vitro and actual malignant myeloma carcinoma tumor development in vivo in warm blooded animals.

The disease of cancer results from development of malignant tumors. A vast amount of medical research has been committed to reducing and overcoming the scourge of cancer. To date, a cure for cancer has not been found. However, much has been learned of the mechanism by which warm blooded animals avoid affliction with cancer. The present invention builds on this knowledge to provide a material which inhibits tumor development and a method for inhibiting such development.

BACKGROUND

Among the cells contained in mammalian body fluids are lymphocytes, monocytes, macrophages and polymorphonuclar cells. These cells act as a natural surveillance system against tumor development in lower mammals, such as rodents up to humans. In recent years, it has been observed that a particular subpopulation of lymphocytes or lymphoid cells, termed "Natural Killer" or "NK" cells, destroy malignant myeloma carcinoma tumor cells and thus prevent development of cancer. The weight of evidence suggests that NK cells possess cytolytic activity related to generation of an active oxygen species such as hydrogen peroxide ($H_2O_2$) or oxygen-containing radicals, e.g. hydroxyl anion ($\cdot OH$) and superoxide anion ($O_2^-$). The NK cells and active oxygen phemonena are described by Herberman et al, Science, Vol. 214, 2 October 1981 pages 24–30, Roder et al, Nature; Vol. 298, 5 August 1982, pages 569–572; Nathan et al, Journal of Immunology, Vol. 129, No. 5, November, 1982 pages 2164–2171; and Mavier et al, Journal of Immunology, Vol. 132, No. 4, April, 1984, pages 1980–1986.

Of course, there are many compounds which release active oxygen species However, that factor alone has not meant that such compound could be introduced into a body to supplement the function of NK cells or where tumor formation is not sufficiently occurring to provide the function of NK cells and inhibit tumor development. Compounds which release active oxygen species generally do so quickly, while effectiveness in supplementing inhibition of malignant myeloma carcinoma tumor development in warm blooded animals such as humans would appear to require at least a slower and more sustained release rate. Until this invention, this had not been effectively achieved. When oxygen release is too fast both tumorous and normal cells may be attacked.

In U.S. Pat. No.4,041,149, granted August 9, 1977, to myself and co-inventors, a composition was described in various forms, including as a dental tablet, which inhibited formation of mouth odor in which the active ingredient was a peroxydiphosphate. Peroxydiphosphate compound differs from most oxygen providing compounds in that it does not provide an initial burst of hydrogen peroxide. Rather, it releases hydrogen peroxide slowly such that when equivalent concentrations are compared to hydrogen peroxide, the amount of oxygen released by the peroxydiphosphate is one-tenth the amount of available oxygen released by hydrogen peroxide. Moreover, only about 50% of the active oxygen is released in 20 hours at 25° C. in the presence of alkaline phosphatase or acid phosphatase each of which is present in the bodies of warm blooded animals, including mice, rats, humans, etc.

ADVANTAGES

It is an advantage of this invention that tumor development is inhibited on tumor cells in vitro and supplementation of inhibition in actual malignant myeloma carcinoma malignant tumor development in vivo in warm blooded animals, such as rodents ranging up to humans.

It is a further advantage of this invention that methods are provided for inhibiting tumor formation by introducing a slow oxygen releasing material into a living host.

SUMMARY

In accordance with certain of its aspects, this invention relates to a composition comprising a dosage amount of about 0.1–10% of a non-toxic water-soluble pharmaceutically acceptable compound derivative of peroxydiphosphoric acid dissolved or dispersed in a pharmaceutical carrier.

In accordance with certain of its further aspects, this invention relates to a method of supplementing inhibition of malignant myeloma carcinoma tumor cells in which a composition comprising a non-toxic dosage amount of about 0.1–6 gm per kg body weight of a warm blooded animal of a non-toxic water-soluble pharmaceutically acceptable compound derivative of peroydiphosphoric acid dissolved or dispersed within a pharmaceutical carrier is administered to a warm blooded animal host by oral ingestion in a regimen which provides about 0.1–6 gm per kg body weight of said warm blooded animal per day.

In accordance with certain of its further aspects this invention relates to a method of supplementing inhibition of malignant myeloma carcinoma tumor formation in which a composition comprising a non-toxic dosage amount of about 0.1–2 gm per kg body weight of a warm blooded animal having malignant myeloma carcinoma tumor cells of a non-toxic water-soluble pharmaceutically acceptable compound derivative of peroxydiphosphoric acid dissolved or dispersed in a pharmaceutical carrier is administered systemically to a warm blooded animal host in a regimen which provides about 0.1–2 gm per kg body weight of said warm blooded animal.

DETAIL

The peroxydiphosphate compound (PDP) is in the form of a non-toxic pharmaceutically acceptable compound, which goes beyond salt indicated in earlier mentioned U.S. Pat. No. 4,041,149. Compounds include alkali metal (e.g. lithium, sodium and potassium) alkaline earth metal (e.g. magnesium, calcium and strontium), zinc and tin salts as well as organic peroxydiphosphate $C_{1-12}$ alkyl, adenylyl, guanylyl, cytosylyl and thymylyl esters and also guaternary ammonium and the like salts. Alkali metal, particularly potassium salt is preferred from among the inorganic cations. The tetrapotassium peroxydiphosphate is a stable, odorless, finely divided, free-flowing, white non-hygroscopic crystalline solid having a molecular weight of 346.35 and an active oxygen content of 4.6%. Tetrapotassium peroxydiphosphate is 47-51% water-soluble at 0°-61° C., but insoluble in common solvents such as acetonitrile, alcohols, ethers, ketones, dimethyl formamide, dimethyl sulfoxide, and the like. A 2% aqueous solution has a pH of about 9.6 and a saturated solution thereof a pH of about 10.9. A 10% solution in water at 25° C. showed no active oxygen loss after four months; and at 50° C. a 10% solution showed an active oxygen loss of 3% in 6 months.

The organic salts can be particularly suitable for administration for supplementing inhibition of formation of malignant myeloma carcinoma tumor cells in a warm blooded animal. From among the organic esters those providing hydrophobic properties such as $C_{1-12}$ alkyl radical and those which facilitate the rapid uptake of peroxydiphosphate moiety by the cells, such as adenylyl, guanylyl, cytosylyl and thymylyl, esters are preferred.

Pharmaceutical carriers suitable for oral ingestion are coated tablets composed of material which resists breakdown by gastric acids in the stomach pH (about 1-3) since peroxydiphosphate would be inactivated by such gastric acids. Rather, the carriers, with tableted granules of the peroxydiphosphoric acid salt solid material therein, are dissolved by intestinal fluids which have a higher pH (about 5.5-10) and do not inactivate the peroxydiphosphate, leaving it subject to enzymatic action by phosphatase present in humans or other warm blooded animals. A desirable tablet coating solution is composed of a fatty acid ester such as N-butyl stearate (typically about 40-50, preferably about 45 parts by weight), wax such as carnuba wax (typically about 15-25, preferably about 20 parts by weight), fatty acid such as stearic acid (typically about 20-30 parts, preferably 25 parts by weight) and cellulose ester, such as cellulose acetate phthalate (typically about 5-15, preferably about 10 parts by weight) and organic solvent (typically about 400-900 parts). Other desirable coating materials include shellac and copolymers of maleic anhydride and ethylenic compounds such as polyvinyl methyl ether. Such coatings are distinct from tablets which are broken down in the oral cavity in which the tablet material typically contains about 80-90 parts by weight of mannitol and about 30-40 parts by weight of magnesium stearate.

Tabletted granules of the peroxydiphosphate salt are formed by blending about 30-50 parts by weight of the peroxydiphosphate salt with about 45-65 parts by weight of a polyhydroxy sugar solid such as mannitol and wetting with about 20-35 parts by weight of a polyhydroxy sugar compound solution such as sorbitol, screening to size blending with about 20-35 parts by weight of a binding agent such as magnesium stearate and compressing the granules into tablets with a tablet compressing machine. The tabletted granules are coated by spraying a foam of a solution of the coating material thereon and drying to remove solvent. Such tablets differ from dental tablets which are typically compressed granules without a special protective coating.

An effective dosage of administration of peroxydiphosphate with a prescribed regimen, when administration is by oral ingestion, is about 0.1-6 gm per kg of body weight daily; when administration is systemic, such as by intramuscular, intraperitoneal or intravenous injection, the dosage is about 0.1-2 gm per kg of body weight daily.

Physiologically acceptable pyrogen-free solvents are suitable carriers for use in the art-recognized manner for systemic administration. Saline solution buffered with phosphate to a physiological pH of about 7 to 7.4 is the preferred carrier for systemic administration. Such solvents are distinct from water-humectant vehicles typically used in dentifrices. Such solution is typically prepared by sterilizing deionized distilled water, checking to insure non-pyrogenicity using the Limulus amebocyte lysate (LAL) test described by Tsuji et al in "Pharmaceutical Manufacturing", October, 1984, pages 35-41, and then adding thereto a phosphate buffer (pH e.g. about 8.5-10) made in pyrogen free sterile water and about 1-100 mgs. peroxydiphosphate compound derivative and sodium chloride to a concentration of about 0.5-1.5% by weight. The solution can be packed in vials for use after being resterilized by passing through a micropore filter. As alternatives, other solutions such as Ringer's solution containing 0.86% by weight sodium chloride, 0.03% by weight potassium chloride and 0.033% by weight calcium chloride may be used.

Peroxydiphosphate compound (PDP) release hydrogen peroxide slowly in the presence of phosphatase enzymes in accordance with the following equation:

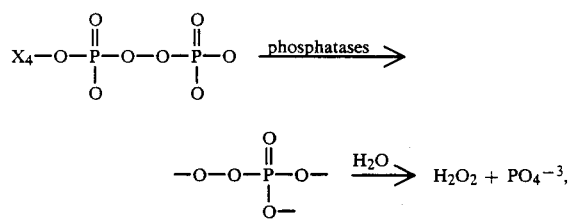

wherein X is a non-toxic pharmaceutically acceptable cation. Phosphatase to break down the peroxydiphosphate is present in saliva as well as in plasma, intestinal fluids and white blood cells. The slow oxygen release is particularly effective in supplementing the inhibition of NK cells against malignant myeloma carcinoma tumor cells which respond to peroxydiphosphate therapy. When warm blooded animals are treated with PDP in accordance with the present invention it is desirable to provide a regimen whereby treatment continues at least until tumors are regressed.

The following comparative examples illustrate the invention. All amounts are by weight unless otherwise indicated.

EXAMPLES

Example 1: In Vitro Study of PDP Tumor Cytotoxicity

In this study the effects of PDP are examined at different concentrations on the growth of murine myeloma (SP$_2$ line) cells (Table 1). Human gingival fibroblasts are used as normal cells control (Table 2). The cells are grown in Dulbecco's modified Eagles's medium supplemented with 10% fetal bovine serum, 1X MEM vitamins, 1XL-glutamine, 1X NEAA$_3$, 1X gentamycin. They are incubated at 37° C. in a humidified $CO_2$ atmosphere. Approximately 1 to $3 \times 10^5$ cells are put into each well of a 24 well microtiter plate containing 2 ml of the medium. PDP (potassium salt) in varying concentrations, is added.

After incubation, the cell viability is determined by removing aliquots from the wells over the time specified in Table 1. The viability is assessed by the trypan blue exclusion test. Fresh medium is added in each well, each day to maintain the necessary growth conditions. The inhibition was calculated by comparing & of cells alive in phosphate buffer saline (PBS) vs. PDP. the data is summarized in Table 1.

TABLE 1
EFFECTS OF PDP ON MURINE MYELOMA (SP$_2$ LINE) CELLS

| TREATMENT | N | NUMBER OF CELLS × 10$^5$ (AT 72 HOURS) | % VIABLE CELLS |
|---|---|---|---|
| Control (PBS) | 4 | 8.98 ± 0.14 | 100% |
| PDP pH 7.0 | | | |
| 100 mcg/ml | 4 | 1.86 ± 0.14 | 47 |
| 500 mcg/ml | 4 | 1.33 ± 0.03 | 33 |
| 1000 mcg/ml | 4 | 1.07 ± 1.17 | 29 |
| 2500 mcg/ml | 4 | 0.48 ± 0.15 | 12 |

These results show that compared to the buffer control, potassium salt of PDP is highly cytotoxic and inhibitative to the murine myeloma (cancer) cells. Table 2 describes the effects on normal cells (human gingival fibroblast).

TABLE 2
EFFECTS ON PDP ON HUMAN GINGIVAL FIBROBLAST

| TREATMENT | N | NUMBER OF VIABLE CELLS × 10$^5$ (AT 72 HOURS) | % VIABLE CELLS |
|---|---|---|---|
| Control (PBS) | 4 | 2.67 ± 0.17 | 100 |
| PDP pH 7.0 | | | |
| 100 mcg/ml | 4 | 2.61 ± 0.16 | 98 |
| 500 mcg/ml | 4 | 2.58 ± 0.13 | 97 |
| 1000 mcg/ml | 4 | 2.12 ± 0.15 | 79 |
| 2500 mcg/ml | 4 | 1.97 ± 0.11 | 74 |

The data in Table 2 suggest no significant effect on cell growth at 100-500 mcg/ml of PDP but that even on normal cells, viability is reduced at 1000 and 2500 mcg/ml. It is noteworthy that the effect on the myeloma tumor cells (Table 1) even at high concentrations is more pronounced than the effect with the normal cells (Table 2).

Similar results are obtained with lithium, sodium, magnesium, calcium, strontium, zinc and stannous salts of PDP, organic peroxydiphosphate as well as $C_{1-12}$ alkyl, adenylyl, guanylyl, cytosylyl, thymylyl esters and tetramethyl ammonium salt of PDP.

EXAMPLE 2: The Effects of PDP, Potassium Pyrophosphate (KPP) and PBS (Phosphate Buffered Saline) on Tumor Development in Vivo Seventy five genetically identical Balb/C mice having an average weight of 20 grams±3 grams groups of 25 animals each: (a) control treated with phosphate buffer saline (PBS); (b) treated with potassium peroxydiphosphate (PDP) and PBS, pH 7.0; and (c) potassium pyrophosphate (KPP) and PBS as a phosphate control. Each animal receives 0.2 ml of Pristane intraperitoneally (I.P.) to prime animals for malignant SP$_2$ cells (murine myeloma carcinoma tumor cells) implantation. After three weeks, the animals are put on oral ingestion treatment regime as follows: Group (a) receiving via I.P. 0.2 ml of PBS; group (b) receiving 2.0 mg PDP suspended in 0.2 ml. of PBS, and group (c) receiving 2.0 mg, of KPP in 0.2 ml of PBS, for three consecutive days. Forty-eight hours after the third injection, each animal is inoculated (I.P.) with 2 to $3 \times 10^6$ cells of SP$_2$ (mice tumor cells, murine myeloma). Thereafter, the animals are given their respective materials, once daily for 5 days/week. That is, (a) PBS, (b) PDP or (c) KPP. The animals are scored for tumor development and death each week. The data is analyzed using the Mantel-Haenszel procedure (Statistical Aspects of the Analysis of Data from Retrospective Studies of Disease, J. National Cancer Institute, Vol. 3, 719-748, 1959). The data in Tables 3, 4 and 5 indicate that PDP is significantly effective in controlling tumor development in mice when compared to PBS or KPP, thereby evidencing that the effects in inhibiting tumor development is due to the provision of active oxygen species and not phosphate.

TABLE 3
PBS* VS. KPP**
TEN WEEK TUMOR DEVELOPEMENT STUDY

| WEEK | TREATMENT | TUMOR AND DEATH | NO TUMOR | AT RISK |
|---|---|---|---|---|
| 1-4 | PBS | 11 | 14 | 25 |
|  | KPP | 10 | 15 | 25 |
| 5 | PBS | 4 | 10 | 14 |
|  | KPP | 4 | 11 | 15 |
| 6 | PBS | 5 | 5 | 10 |
|  | KPP | 2 | 9 | 11 |
| 7 | PBS | 2 | 3 | 5 |
|  | KPP | 4 | 5 | 9 |
| 8 | PBS | 0 | 3 | 3 |
|  | KPP | 1 | 4 | 5 |
| 9 | PBS | 2 | 1 | 3 |
|  | KPP | 3 | 1 | 4 |
| 10 | PBS | 1 | 0 | 1 |
|  | KPP | 0 | 1 | 1 |

*PBS=Phosphate buffer saline
**KPP=Putassium pyrophosphate

Mantel-Haenszel chi-square=0.36 with 1, d.f., P=0.55

Odds ratio=1.34

These results are not significant and evidence no significant difference between PBS and DPP in reducing tumor development in the animals.

TABLE 4
TEN WEEK TUMOR STUDY
PBS* VS. PDP**

| WEEK | TREATMENT | TUMOR AND DEATH | NO TUMOR | AT RISK |
|---|---|---|---|---|
| 1-4 | PBS | 11 | 14 | 25 |
|  | PDP | 2 | 23 | 25 |
| 5 | PBS | 4 | 10 | 14 |
|  | PDP | 4 | 19 | 23 |

TABLE 4-continued

TEN WEEK TUMOR STUDY PBS* VS. PDP**

| WEEK | TREATMENT | TUMOR AND DEATH | NO TUMOR | AT RISK |
|---|---|---|---|---|
| 6 | PBS | 5 | 5 | 10 |
|   | PDP | 5 | 14 | 19 |
| 7 | PBS | 2 | 2 | 5 |
|   | PDP | 2 | 13 | 14 |
| 8 | PBS | 0 | 3 | 3 |
|   | PDP | 2 | 10 | 12 |
| 9 | PBS | 2 | 1 | 3 |
|   | PDP | 3 | 7 | 10 |
| 10 | PBS | 1 | 0 | 1 |
|    | PDP | 1 | 6 | 7 |

*PBS=Phosphate buffer saline
**PDP=Putassium peroxydiphosphate

Mantel-Haenszel chi square=10.40 with 1, d.f., P=0.001.

Odds ratio=3.66.

These data indicate that the PBS control group develop tumors significantly sooner than PDP treated animals (P=0.001).

TABLE 5

TEN WEEK TUMOR STUDY KPP* VS. PDP***

| WEEK | TREATMENT | TUMOR AND DEATH | NO TUMOR | AT RISK |
|---|---|---|---|---|
| 1-4 | KPP | 10 | 15 | 25 |
|     | PDP | 2 | 23 | 25 |
| 5 | KPP | 4 | 11 | 15 |
|   | PDP | 4 | 19 | 23 |
| 6 | KPP | 2 | 9 | 11 |
|   | PDP | 5 | 14 | 19 |
| 7 | KPP | 4 | 5 | 9 |
|   | PDP | 2 | 14 | 14 |
| 8 | KPP | 1 | 4 | 5 |
|   | PDP | 2 | 10 | 12 |
| 9 | KPP | 3 | 1 | 4 |
|   | PDP | 3 | 7 | 10 |
| 10 | KPP | 0 | 1 | 1 |
|    | PDP | 1 | 6 | 7 |

*KPP=Putassium pyrophosphate
**PDP=Putassium peroxydiphosphate

Mantel-Haenszel chi square=5.86 with 1, d.f., P=0.02.

Odds ratio=2.60.

The data indicated that the DPP group develops tumors significantly sooner than PDP treated animals (P=0.001).

Similar results can be observed when each of PBS, DPP and PDP are administered intramuscularly and intravenously in the same concentrations in PBS or orally in a concentration of 1 mg/ml (0.1%) in a stable carrier of 45 parts of N-butyl stearate, 20 parts of carnauba wax, 25 parts of stearic acid and 10 parts of cellulose acetate phthalate.

Similar results are obtained with other inorganic salts of PDP, particularly lithium, sodium, magnesium, calcium, strontium, zinc and stannous salts. Organic compounds of PDP, particularly $C_{1-12}$ alkyl, adenylyl, guanylyl, cytosylyl, thymylyl esters and tetramethyl ammonium salts are also effective in countering growth of murine myeloma malignant tumor cells.

EXAMPLE 3

500 parts of potassium peroxydiphosphate and 641 parts of mannitol are blended and wet with 32.5 parts of a 10% solution of sorbitol to form a wet granulate, which is dried at 49° C. and screened through a 12 mesh, U.S. sieve (1.68 mm screen openings) 35 parts of magnesium stearate is then added as a binder and tabletted granules are formed by compressing the composition on a tablet compressing machine.

The tablets are coated with an enteric coating solution of the following composition:

| Cellulose acetate phthalate | 120 parts |
|---|---|
| Carnauba wax | 30 parts |
| Stearic acid | 10 parts |
| 95% ethanol | 450 parts |
| Acetone | Q.S. to 1000 parts |

The coating is carried out by a pouring procedure in a conventional coating pan.

When the tablets thus formed are ingested, they pass through the stomach without breakdown and the coating is then dissolved by intestinal fluids.

EXAMPLE 4

Deionized distilled water is stabilized at atmospheric pressure for 20 minutes in an autoclave. After cooling, it is tested for non-pyrogenicity using the Limulus Amebocyte Lysate (LAL) as described by Tsuji et al in "Pharmaceutical Manufacturing" October, 1984, pages 35-41. 50 parts of potassium peroxydiphosphate, sodium chloride in amount corresponding to 0.9% of solution and 0.1 M phosphate buffer containing $KH_2PO_4$, and $Na_2HPO_4$, pH 9.4 are added to the pyrogen-free sterile water. The solution is then sterilized by passing it through a 0.5 micropore filter and is then packed in sterile files.

Although the invention has been described with reference to specific examples, it will be apparent to one skilled in the art that various modifications can be made thereto which fall within its scope.

I claim:

1. A method of supplementing inhibition of formation of malignant murine myeloma carcinoma tumor cells in a warm blooded animal by lymphocyte natural killer cells in which a composition comprising about 0.1-6 gm per kg body weight of a warm blooded animal of a non-toxic water-soluble pharmaceutically acceptable compound derivative of peroxydiphosphoric acid, which compound derivative is a salt selected from the group consisting of alkali metal, alkaline earth metal, zinc and tin or is selected from the group consisting of $C_{1-12}$ alkyl, adenylyl, guanylyl, cytosylyl and thymylyl esters or quaternary ammonium salt, dissolved or dispersed with a pharmaceutical carrier which is a coated tablet which resists breakdown by gastric acids while being broken down by intestinal fluid at a pH of about 5.5 to 10 is administered to a warm blooded animal host by oral ingestion in a regimen which provides about 0.1-6 gm per kg body weight of said warm blooded animal per day whereby phosphatase enzyme present in saliva, plasma, intestinal fluids and white blood cells in said warm blooded animal reacts with said peroxydiphosphate compound to release hydrogen peroxide slowly and thereby supplement the inhibition of said malignant tumor cells in said warm blooded animal which is effected by said lymphocyte natural killer cells.

2. A method of supplementing inhibition of formation of malignant murine myeloma carcinoma tumor cells in a warm blooded animal by lymphocyte natural killer cells in which a composition comprising about 0.1-2 gm per kg body weight of a warm blooded animal of a non-toxic water-soluble pharmaceutically acceptable compound derivative of peroxydiphosphoric acid, which compound derivative is a salt selected from the group consisting of alkali metal, alkaline earth metal, zinc and tin or is selected from the group consisting of $C_{1-12}$ alkyl, adenylyl, guanylyl, cytosylyl and thymylyl esters or quaternary ammonium salt, dissolved or dispersed within a pharmaceutical carrier which has a physiological pH of about 7.0 to 7.4 is administered systemically to a warm blooded animal host in a regimen which provides about 0.1-2 gm per kg body weight of a warm blooded animal per day whereby phosphatase enzyme present in saliva, plasma, intestinal fluids and white blood cells in said warm blooded animal reacts with said peroxydiphosphate compound to release hydrogen peroxide slowly and thereby supplement the inhibition of said malignant tumor cells in said warm blooded animal which is effected by said lymphocyte natural killer cells.

3. The method claimed in claim 2 wherein said physiologically acceptable pyrogen-free solvent is a buffered phosphate saline solution.

4. A method of supplementing inhibition of formation of malignant myeloma carcinoma tumor cells in a warm blooded animal by lymphocyte natural killer cells in which a composition comprising about 0.1-6 gm per kg body weight of a warm blooded animal of a non-toxic water-soluble pharmaceutically acceptable compound derivative of peroxydiphosphoric acid, which compound derivative is a salt selected from the group consisting of alkali metal, alkaline earth metal, zinc and tin or is selected from the group consisting of $C_{1-12}$ alkyl, adenylyl, guanylyl, cytosylyl and thymylyl esters or quaternary ammonium salt, dissolved or dispersed with a pharmaceutical carrier which is a coated tablet which resists breakdown by gastric acids while being broken down by intestinal fluid at a pH of about 5.5 to 10 is administered to a warm blooded animal host by oral ingestion in a regimen which provides about 0.1-6 gm per kg body weight of said warm blooded animal per day whereby phosphatase enzyme present in saliva, plasma, intestinal fluids and white blood cells in said warm blooded animal reacts with said peroxydiphosphate compound to release hydrogen peroxide slowly and thereby supplement the inhibition of said malignant tumor cells in said warm blooded animal which is effected by said lymphocyte natural killer cells.

5. The method claimed in claim 4 wherein the coating of said tablet comprises about 40-50 parts by weight of N-butyl stearate, about 15-25 parts by weight of carnauba wax, about 20-30 parts by weight of stearic acid and about 5-15 parts by weight of cellulose acetate phthalate.

6. The method claimed in claim 4 wherein said non-toxic, water-soluble pharmaceutically acceptable compound derivative of peroxydiphosphoric acid is a salt selected from the group consisting of alkali metal, alkaline earth metal, zinc and tin.

7. The method claimed in claim 6 wherein said salt is potassium peroxydiphosphate.

8. The method claimed in claim 4 wherein said non-toxic water-soluble pharmaceutically acceptable compound derivative of peroxydiphosphoric acid is selected from the group consisting of $C_{1-12}$ alkyl, adenylyl, guanylyl and cytosylyl, thymylyl esters, or quaternary ammonium salt.

9. The method claimed in claim 8 wherein said compound derivative is a $C_{1-12}$ alkyl ester of peroxydiphosphoric acid.

10. The method claimed in claim 8 wherein said compound derivative is adenylyl, guanylyl, cytosylyl, or thymylyl ester of peroxydiphosphoric acid.

11. A method of supplementing inhibition of formation of malignant myeloma carcinoma tumor cells in a warm blooded animal by lymphocyte natural killer cells in which a composition comprising about 0.1-2 gm per kg body weight of a warm blooded animal of a non-toxic water-soluble pharmaceutically acceptable compound derivative of peroxydiphosphoric acid, which compound derivative is a salt selected from the group consisting of alkali metal, alkaline earth metal, zinc and tin or is selected from the group consisting of $C_{1-12}$ alkyl, adenylyl, guanylyl, cytosylyl and thymylyl esters or quaternary ammonium salt, dissolved or dispersed within a pharmaceutical carrier which has a physiological pH of about 7.0 to 7.4 is administered systemically to a warm blooded animal host in a regimen which provides about 0.1-2 gm per kg body weight of a warm blooded animal per day whereby phosphatase enzyme present in saliva, plasma, intestinal fluids and white blood cells in said warm blooded animal reacts with said peroxydiphosphate compound to release hydrogen peroxide slowly and thereby supplement the inhibition of said malignant tumor cells in said warm blooded animal which is effected by said lymphocyte natural killer cells.

12. The method claimed in claim 11 wherein said non-toxic water-soluble pharmaceutically acceptable compound derivative of peroxydiphosphoric acid is a salt selected from the group consisting of alkali metal, alkaline earth metal, zinc and tin.

13. The method claimed in claim 12 wherein said salt is potassium peroxydiphosphate.

14. The method claimed in claim 11 wherein said non-toxic water-soluble pharmaceutically acceptable compound derivative of peroxydiphosphoric acid is selected from the group consisting of $C_{1-12}$ alkyl, adenylyl, guanylyl, cytosylyl and thymylyl ester or quaternary ammonium salt.

15. The method claimed in claim 14 wherein said compound derivative is a $C_{1-12}$ alkyl salt of peroxydiphosphoric ester.

16. The method claimed in claim 14 wherein said compound derivative is adenylyl, guanylyl, cytosylyl, or thymylyl ester of peroxydiphosphoric acid.

* * * * *